United States Patent [19]

Balocco

[11] Patent Number: 5,308,246
[45] Date of Patent: May 3, 1994

[54] VISUALIZATION TRAINING DEVICE WITH ADJUSTABLE ELECTRO-OPTICAL SHUTTER

[76] Inventor: Mark E. Balocco, 545 Shell Pkwy., Apt. 3211, Redwood City, Calif. 94065

[21] Appl. No.: 605

[22] Filed: Jan. 5, 1993

[51] Int. Cl.⁵ .............................. G09B 19/00
[52] U.S. Cl. ...................... 434/236; 359/83; 351/44
[58] Field of Search .............. 434/236, 433; 351/158, 351/44, 45; 359/83, 84

[56] References Cited

U.S. PATENT DOCUMENTS

| | | | |
|---|---|---|---|
| 3,910,690 | 10/1975 | Regan | 351/31 |
| 3,942,270 | 3/1976 | Hoyt et al. | 359/84 X |
| 4,106,217 | 8/1978 | Witt | 434/36 |
| 4,424,529 | 1/1984 | Roese et al. | 358/88 |
| 4,435,047 | 3/1984 | Fergason | 350/334 |
| 4,482,326 | 11/1984 | Witt | 359/84 X |
| 4,522,474 | 6/1985 | Slavin | 351/203 |
| 4,550,990 | 11/1985 | Trispel et al. | 351/243 |
| 4,698,668 | 10/1987 | Milgram | 358/92 |
| 4,699,470 | 10/1987 | McLaughlin et al. | 350/334 |
| 4,726,673 | 2/1988 | Blankenhorn | 351/238 |
| 4,866,285 | 9/1989 | Simms | 250/495.1 |
| 4,940,323 | 7/1990 | Downing | 351/203 |
| 4,992,201 | 2/1991 | Pearlman | 252/299.1 |
| 5,002,387 | 3/1991 | Baljet et al. | 352/63 |
| 5,010,230 | 4/1991 | Uemura | 219/121.62 |
| 5,026,151 | 6/1991 | Waltuck et al. | 351/246 |

FOREIGN PATENT DOCUMENTS 2530039  1/1984  France ................ 351/158

*Primary Examiner*—Gene Mancene
*Assistant Examiner*—Jeffrey A. Smith
*Attorney, Agent, or Firm*—David Pressman

[57] ABSTRACT

A visualization training device with adjustable electro-optical shutters comprises a pair of goggles (10) and a control unit (20). The goggles have a single lens made of an electro-optical shutter (11) which uses liquid crystals as the light valve. The control unit produces a square wave which alternately drives the shutter opened and closed. The opening and closing cycles are adjustable in duty cycle and frequency via a duty cycle control knob (21) and a frequency control knob (22). When the shutter is opened, it is transparent so that the user has a panoramic view of external visual information. When the shutter is closed, it becomes an opaque white to occlude the visual information from the user, so that the user must mentally visualize the previous information. The opening and viewing, and closing and visualizing cycle is repeated to train and improve the visualization ability of the user.

4 Claims, 2 Drawing Sheets

VISUALIZATION TRAINING DEVICE WITH ADJUSTABLE ELECTRO-OPTICAL SHUTTER

BACKGROUND

1. Field Of The Invention

The present invention relates generally to devices for visualization training, specifically by interrupting the visual field of a user with a shutter.

2. Prior Art

In the past, the field of psychology has addressed many issues regarding the brain and its functioning. How it works and how it can be improved has been the focus of many areas of study. The brain has the ability to process 30 billion bits of information per second. However, even with our present understanding of the mind, we are still unable to fully tap the brain's vast potential. An area of brain function that is of vital importance is visualization or imagery. Visualization is the ability to "see" or imagine images with the mind alone, without input from the eyes. For example, one can visualize the experience of driving a racing car, scenes of a movie being made, a new aircraft design, or the experience of a personal relationship. Therefore, visualization is a vital part of creativity, imagination, and memory. Consequently, if our visualization skills can be improved, then our creativity, imagination, and memory can also be enhanced.

Ironically, the ability to use the eyes to see information can be as much of a disadvantage to learning as it is beneficial. Without doubt, the eyes are one of our most important senses. They are used extensively as an "input device" to the brain. However, relying too much on the eyes reduces the need for the brain to visualize and memorize information. For example, if visual information is viewed by the eye for an unlimited amount of time, there is no need to remember or recall this information. In fact, relying on vision to obtain information prevents the brain from being improved. Therefore, the solution is to reduce our reliance on our visual sense, forcing the brain to rely more on visualization and memory. As a result, these skills are exercised and improved. After all, muscles should be exercised and developed. Similarly, the brain should also be exercised regularly for its continued development.

Visualization techniques have been used for many years for different applications. Psychiatrists use a form of visualization, hypnosis, for purposes ranging from curing depression to helping crime witnesses recall their experiences. Terminally ill patients have been known to "mysteriously" cure themselves by visualizing or imagining getting well. Artists visualize or imagine their work before expressing their images on canvas, stone, or metal. Athletes, especially those who follow predetermined programs, such as skaters and skiers, visualize their performance repeatedly prior to competition as a form of practice. Napoleon fought battles in his mind, then found that the visualization made real battles easier to win. Albert Einstein said, "Visualization is more important than knowledge." He also said that he visualized riding on the end of a light beam to help him develop the theory of relativity. Obviously, a wide range of activities can greatly benefit from visualization.

Visualization can also help to improve memory as well. The recall of information, or memory, is often in the form of visual images. The mind's "eye" must first see the image before the person can remember. Therefore, if the ability to visualize is increased, the ability to remember should also be increased. According to a college textbook, "Imagery facilitates the teaming of information and produces good recall performances. Subjects taught to make up strange visual images of the material to be learned perform at a much higher level than subjects who do not use images. Presumably, encoding words as images somehow enhances the storage of the items in long-term memory. For hundreds of years memory experts have relied heavily on visual images to improve their performances." Lyle E. Boume, Jr. and Bruce R. Ekstrand, *Psychology: Its Principles And Meanings.* Fourth Edition, (New York: CBS College Publishing, 1982), page 155.

A visualized picture or image that is as clear as reality is referred to as hallucination. The brain cannot distinguish between what is vividly imagined, or hallucinated, from what is real. The ability of the brain to create such a "virtual reality" has been studied by using the technique of sensory deprivation. According to Dr. William Fezler, "Studies in the area of sensory deprivation provide even more data to substantiate that your imagery can be as vivid as reality. It was shown, for example, that if you remove the real world (outside), an imaginary (inside) one as real in appearance will soon materialize. Researchers sensorially deprived subjects, [i.e., they] removed the outside world, with a number of devices. They put halved ping-pong balls over the eyes to remove vision. The body was bound to eliminate touch. Nose, mouth, and ears were plugged to eradicate smell (and breathing!), taste, and hearing. Within six hours a whole new experience, graphic in all five senses, materialized. When the world was taken away, subjects created their own! You have the power to imagine so vividly that you can't tell your image from reality. This is the first major step to creation." William Fezler, Ph.D., "Creative Imagery, How to Visualize In AH Five Senses" (N.Y.: Fiveside, 1989, p. 84). Although highly effective, the ping-pong balls are inconvenient and uncomfortable to wear. Furthermore, they will make the users appear very silly indeed.

The Theory Of Props states that the senses can be heightened by plugging in the actual sensory experience while practicing visualization. According to personal development coach and author of the bestseller *Unlimited Power,* Anthony Robbins: "Most peoples' pictures are not that clear, although they could be. All you have to do is practice. And, how do you practice? Well, you don't try to master everything overnight. You take a look at somebody's nose, and you focus just on their nose, not their whole face and body. And, you look at it, and then close you eyes, and then you pretend that you are seeing it in you mind. . .Actually look at their nose—open your eyes, see the nose—close your eyes, imagine you're seeing it. You do it over and over until pretty soon you're opening and closing your eyes so fast . . .that your brain doesn't know when you're actually seeing it and when you're making it up, Pretty soon you'll get good at seeing the nose. You'll close your eyes and just be able to picture the nose. Then do nose and eyes. Then, nose, eyes, and mouth and the face and expand until you can see the whole person." Anthony Robbins, Personal Power cassette program (Robbins Research International, 1989). Produced by Guthy-Renker Corp., *Moving Beyond Procrastination To Unlimited Power Anchoring Yourself To Success,* Volume 6 Side 2B.

The Theory Of Props basically requires subjects to perform eye blinking. Subjects look at and study an image for a few seconds. Then, after closing the eyes, they attempt to continue to "see" or visualize the same image with the mind alone. This process is repeated while the rate of eye blinking is increased. The objective is to "trick" the brain into thinking that it is seeing the image when the eyes are closed. This technique helps the brain to develop its visualization skills. However, continued eye blinking can be extremely tiring, while it also cannot eliminate the distraction of the subject's surrounding environment.

Other techniques have also been developed for teaching. For years, flash cards have been used to drill individuals on particular subjects. The intent is to elicit a quick response by presenting questions briefly and rapidly to the individual. The eyes must quickly see what is being presented so the brain can process the information. Therefore, vision is important only for an instant, so that the brain must then focus on a solution to the question at hand. However, small, printed or handwritten flash cards are very limited in the information which can be presented. Furthermore, they cannot prevent the individual from being distracted by the surrounding environment.

Inventions such as tachistoscopes, stroboscopes, and stereoscopic viewers are also used to control the presentation of visual information. Recently, these systems have incorporated electrooptical devices to improve their versatility and performance. All these systems consist of a shuttering device and a control unit for synchronized presentation of visual information. The following is a brief description of these systems and their intended use:

A. Tachistoscopes are for exposing visual stimuli as pictures, letters, or words for extremely brief periods of time. They are used especially for testing perception. U.S. Pat. No. 4,726,673 to Blankenhom (1988) shows a tachistoscope using a pair of electro-optical light valves for wearing over the eyes of a subject. The valves are opened and closed in synchronization with alternating images presented by a television fed by two independent cameras.

B. Stroboscopes are used for studying moving objects, especially those in rapid motion. It synchronizes the cyclic motion of an object with the visual presentation of the object to a viewer. An example is a spinning disk with holes or apertures on the edge through which a moving object is viewed. The rate at which the apertures pass the eyes is synchronized with the repetition rate of a repeating event, such as dripping water. As a result, the moving object will appear to be frozen.

C. Stereoscopic viewing systems are used for conveying depth in two-dimensional images. This is accomplished by viewing two different perspectives of the same scene. Using a display device and two individual electro-optical shutters, one in front of each eye, the different perspectives can be rapidly alternated on a single screen and viewed by the appropriate eye. This yields a three-dimensional picture. The synchronized shutters and alternating perspectives happen so rapidly that the brain sees the two different perspectives at the same time. By displaying two perspectives of each frame in a motion picture, a three-dimensional motion picture will result. Examples of stereoscopic viewing systems are shown in U.S. Pat. Nos. 4,424,529 to Roese et al. (1984), and 4,698,668 to Milgram (1987).

In conclusion, the above techniques are either limited in the range of information that they can present, will quickly cause eye fatigue, or cannot eliminate distracting stimuli in the subject's environment. On the other hand, the above devices must all be linked and synchronized in some way with the information being observed or presented. Because of the need to synchronize the shutter devices to the visual information being presented, the equipment required is relatively complex, expensive, or difficult to use. Therefore, no current technique or device is appropriate for use as an aid for visualization training.

OBJECTS AND ADVANTAGES

In the present invention, a primary object is to provide a visualization training device. Other objects are to provide such a device which enables a user to accept or occlude visual stimulus as an aid for enhancing the user's visualization abilities, to provide the user with an unhindered, panoramic view when seeing; but to occlude the entire field of vision when visualizing.

Additional objects of the present invention are to provide a visualization training device which can use a single shutter (instead of the two required in the prior art), which is simple to operate, which is light in weight and comfortable to wear, and which is simple and economical to manufacture.

Further objects and advantages of the invention will become apparent from a consideration of the drawings and ensuing description.

Figure 1A:
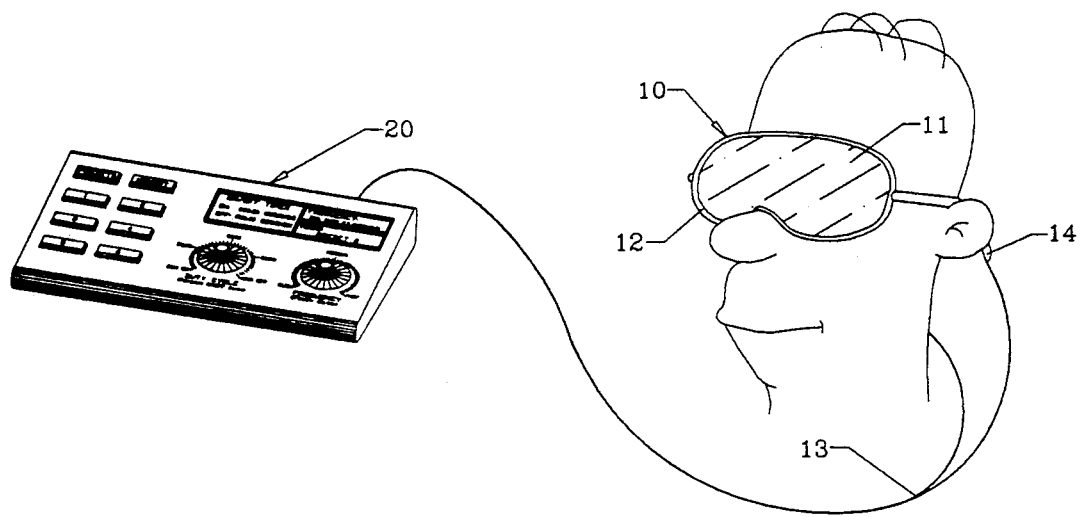
FIGS. 1A and 1B are perspective views of a visualization training device in accordance with a preferred embodiment of the invention.

| Drawing Reference Numerals |
| --- |
| 10. Goggles |
| 11. Shutter |
| 12. Frame |
| 13. Cable |
| 14. Temple Arm |
| 20. Control Unit |
| 21. Duty Cycle Control Knob |
| 22. Frequency Control Knob |
| 23. Preset Buttons |

SUMMARY

According to the invention, visualization training is effected by periodically and automatically interrupting a wearer's vision to force the wearer to periodically visualize. Such interruption can be effected with goggles, a console unit, a computer, etc.

DESCRIPTION—FIGS. 1A AND 1B

Figure 1B:
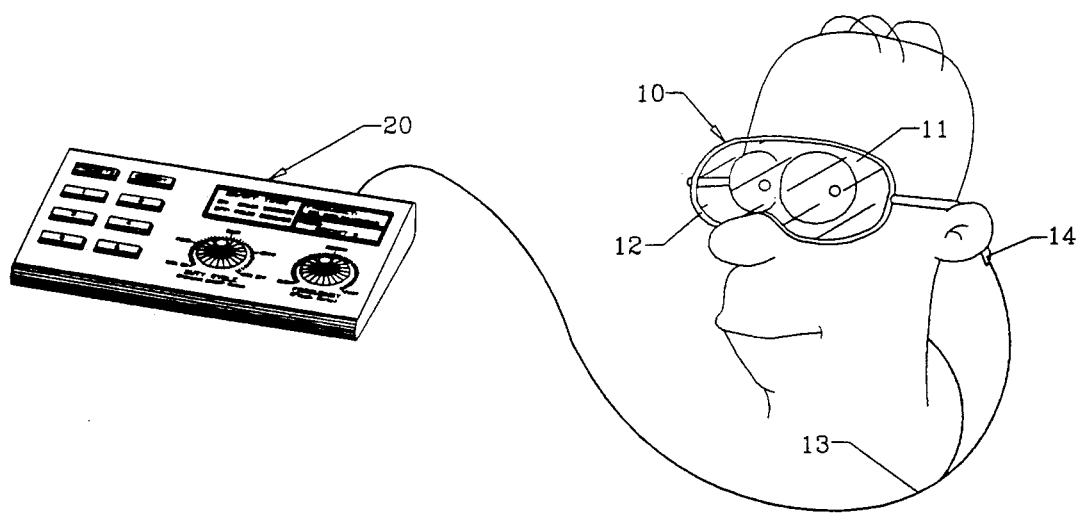

In the embodiment of FIGS. 1A and 1B, a pair of goggles 10 have an adjustable electro-optical shutter, are sunglasses-styled, and are associated with a compact control unit 20. Goggles 10 have a "lens" made of an electro-optical shutter 11 mounted within a frame 12. Shutter 11 is a single pane of conventional liquid crystal light valve similar to the type available at Edmund Scientific Company, Barrington, N.J. This type of light valve is currently used for many applications, including sunroofs for automobiles and windows for buildings. When shutter 11 is in the deenergized or closed state, it has an opaque, milky white appearance which completely blocks the transmission of light, as shown in FIG. 1A. Because shutter 11 is a single pane light valve, it will occlude all visual information simultaneously from both eyes of its wearer or user.

A cable 13 electrically connects shutter 10 with control unit 20, which will be explained later in conjunction with FIG. 2A. The cable is routed through a temple arm 14 of frame 12 to minimize interference with the user.

When an electrical current is supplied to shutter 11 by control unit 20, the shutter will be energized into its opened state, such that it will immediately change from opaque to transparent, as shown in FIG. 1B. As a result, shutter 11 will allow the user an unhindered, panoramic view of the surroundings. When the shutter is opened, it will simply allow the user to look at whatever is in the surroundings. Therefore, unlike the devices discussed in the "Background" section, the visualization training device has no need for any type of connection or coordination with the visual stimulus at all. As a result, it has the advantage of simplicity.

DESCRIPTION—FIGS. 2A TO 2C

Figure 2A:
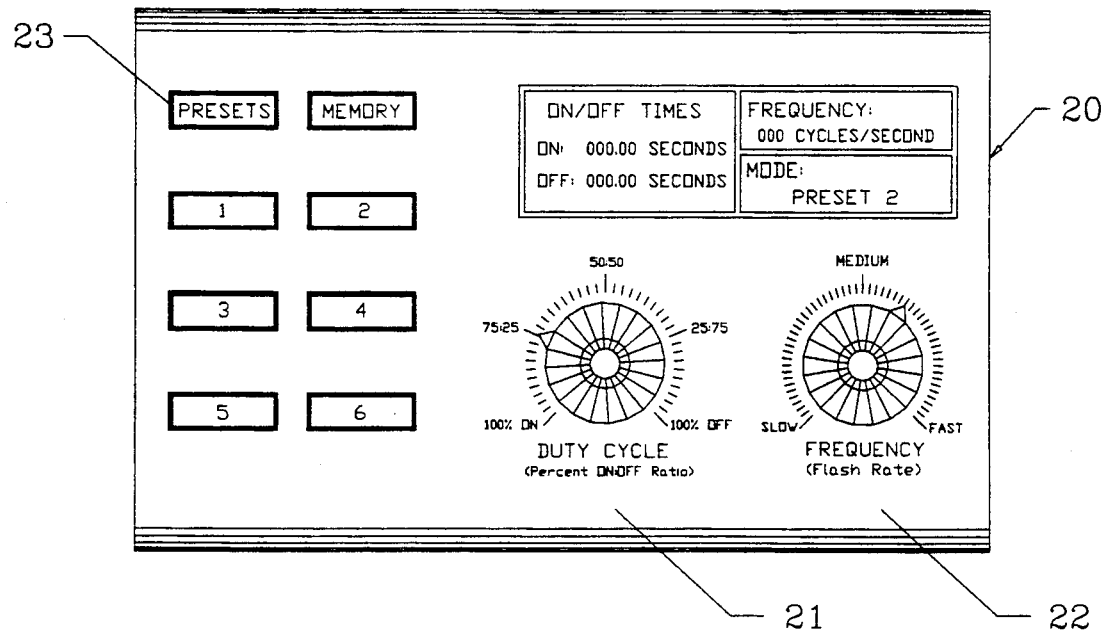
FIG. 2A is a front view of a control unit used in the device of FIGS. 1A and 1B.
Figure 2B:
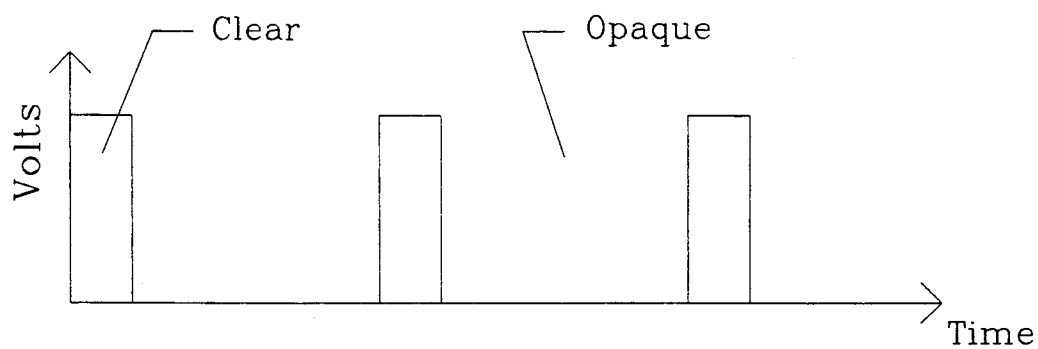
FIGS. 2B and 2C are timing diagrams illustrating the operation of the control unit of FIG. 2A.

A front view of control unit 20 is shown FIG. 2A. The control unit is a conventional square wave generator which produces square waves such as those shown in FIGS. 2B and 2C. Each square wave energizes and opens shutter 11. The shutter will be closed during the periods between the square waves. Control unit 20 has a duty cycle control knob 21 for adjusting the duty cycle, or open versus closed ratio of the shutter. The duty cycle can be infinitely varied from 100% open to 100% closed by turning knob 21 fully counterclockwise or clockwise, respectively. The square wave shown in FIG. 2B has a duty cycle of 20%, which will cause shutter 11 to be clear or open for only 20% of the time, and opaque or closed for 80% of the time. The square wave shown in FIG. 2B has a duty cycle of about 80%, which will cause the shutter to remain clear or open for 80% of the time, and opaque or closed for 20% of the time. Control unit 20 also has a frequency control knob 22 for adjusting the frequency, ranging from slow to fast, of the on and off blinking of shutter 11. The frequency can be varied from 0 Hz to 50 Hz. Also by adjusting the duty cycle to 100% open or 100% closed, the frequency can effectively be reduced to 0 Hz.

Optionally, control unit 20 can offer preset buttons 23. Using suitable memory circuitry, factory or user selected duty cycle and frequency settings can be recalled easily. Different selfings suitable for different training purposes or personal preference may be conveniently selected with the buttons.

Also, optionally, the device can have a remote on/off push button switch so that the user can open the shutter temporarily to "refresh" an image.

OPERATION—FIGS. 1A TO 2C

The psychological effects of the visualization training device are based on the technique of sensory deprivation and the Theory Of Props described in the "Background Of The Invention" section, supra. To reiterate, the technique of visual deprivation teaches that if the brain is deprived the senses and therefore the "real world", it will begin to create its own, imaginary world. Researchers covered the eyes of subjects with ping-pong balls to create the "ganzfeld" effect, an area of white with no visual discrimination or distractions. After a few hours of viewing this white, the subjects experienced brilliant visual hallucinations. The Theory Of Props teaches that, by alternately viewing an object and closing the eyes, or blinking the eyes, the brain will eventually be able to visualize the image of the object even when the eyes are closed.

The visualization training device applies both the technique of sensory deprivation and the theory of props for improving visualization skills. It applies the technique of sensory deprivation by providing an electronically created "ganzfeld" effect. After the user dons lightweight goggle 10, duty cycle control knob 21 is adjusted to produce a 100% duty cycle to maintain shutter 11 in a constantly closed state. When the shutter is closed, as shown in FIG. 1A, all normal visual stimulation will be occluded from the user. Only a field of white can be seen, completely without visual discrimination or distractions. Gradually, the user will begin to visualize and imagine so vividly that the images become indistinguishable from reality. As a result, the skills of visualization and creativity are gradually teamed and improved. This effect is similar to that produced by the ping-pong balls, but the visualization training device is far more convenient, comfortable, and dignified.

Figure 2C:
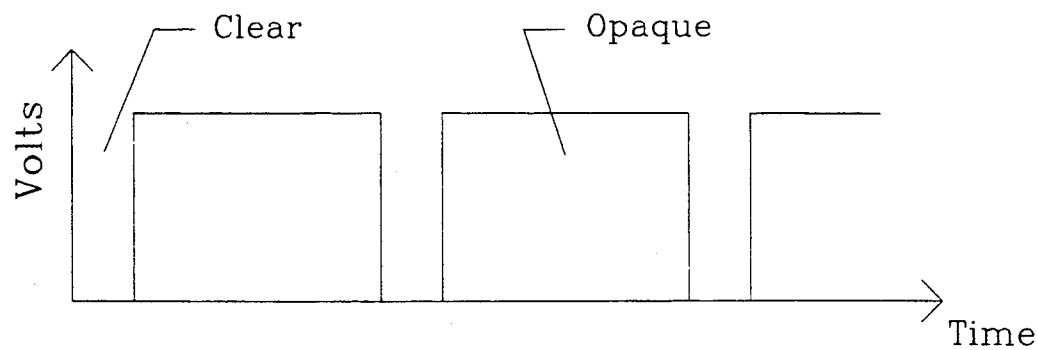

The visualization training device also applies the Theory Of Props by providing electronic "eye blinking." During the beginning of visualization training, frequency control knob 22 on control unit 20 is adjusted to a low frequency, such as 0.5 Hz (one cycle every two seconds), and duty cycle control knob 21 is adjusted to a high duty cycle, as shown in FIG. 2A, such that a square wave similar to that shown in FIG. 2C is produced. Shutter 11 will be caused to blink slowly, but it will remain mostly open during each opening and closing cycle. During each lengthy period when shutter 11 is open, as shown in FIG. 1B, the user will be able to see a panoramic view of the surroundings, or will be able to look at a particular object, such as somebody'nose as described by Anthony Robbins. The long periods during which shutter 11 is open are interspersed with short periods during which shutter 11 is closed, as shown in FIG. 1A. When the shutter is closed, the user can imagine or visualize the continued visual presence of the object. The short shutter closing times will allow the user to be refreshed frequently of the visual stimulus.

Depending upon the user's preference and comfort level, duty cycle control knob 21 can be gradually adjusted for shorter and shorter duty cycles, while frequency knob 22 can be gradually adjusted for higher and higher frequencies, or vice versa. The objective is to train the user to rely more and more on an ability to visualize the image. Preferably, shutter 11 will be closed for longer and longer periods of time, while it is blinked faster and faster. Eventually, the user will be able to easily and vividly visualize or recall the image at will. As a result, visualization and memory skills can be greatly improved.

Optional factory presets 23 will provide convenient frequency and duty cycle settings for novice, amateur, experienced, and expert levels training. For example, the novice level can have very long shutter opening cycles and low frequency, while the expert level can have very short shutter opening cycles and high frequency. Also some of the presets can be user controllable to remember favorable user settings.

SUMMARY, RAMIFICATIONS, and SCOPE

Accordingly the reader will see that I have provided a visualization training device with an adjustable electro-optical shutter which can be used to teach and greatly improve visualization, memory, and other mental skills. This is entirely unlike any other applications in which liquid crystal shutters have been used in the past. It provides a convenient, lightweight, and comfortable method for occluding vision and producing the "ganzfeld" effect. This can help users learn to vividly visualize brilliant images without actual visual stimulation. It provides a convenient and comfortable way for "blinking" visual stimulus on and off without the need for the user to perform tiring eye blinking. This can train users to store information in memory as visual images. It allows the user to vary the duty cycle and frequency of the shutter's blinking with infinite resolution. It provides optional, preselected duty cycle and frequency settings.

While my above descriptions are specific, they should not be construed as limitations on the scope of the invention, but only as examples of the preferred embodiment. Many other variations are possible. For example, a spectacle-like frame with multiple shutters can be used to occlude specific portions of the visual field or to isolate a specific image. Factory presets 23 can be eliminated. Also the shutter can be used in front of just one eye at a time (the other eye can be covered). Further, in lieu of goggles, the shutter can be a large square panel, about 1 meter square, which can be positioned in front of a user, e.g., upright on a desk at which the user is seated. The panel can have hooded sides extending toward the user, or it can be the front of a viewing box, e.g., as shown in Downing U.S. Pat. No. 4,940,323 (1990). The viewing box can include internal images, a video, or photos. Alternatively, the panel can be positioned in front of a television or computer screen. Instead of a separate unit, the control unit can be mounted in so as to be part of goggles 10. In lieu of shutters, the user can be placed in a completely dark room, with optional images on the walls, and a light bulb can be turned on and off to simulate the glasses. No field of white would be provided when the light was off, but visualization would still be stimulated. Also a computer alone (without a screen shutter) can be suitably programmed to simulate the aforedescribed visualization training. Accordingly, the scope of the invention should be not be determined by the embodiments illustrated, but by the appended claims and their legal equivalents.

I claim:

1. A method of training a person to visualize, comprising:

providing said person with a field of view so that said person can view an image in said field of view, periodically interrupting said field of view with a series of sequential interruption intervals so that said person will not see said image during each of said interruption intervals, said periodically interrupting being performed by an electro-optical shutter in front of at least one eye of said person, whereby said person will be forced to visualize said image during each of said interruption intervals.

2. The method of claim 1, further including varying the frequency of said sequential interruption intervals.

3. The method of claim 1, further including varying the duration of said sequential interruption intervals.

4. The method of claim 1, further including varying the frequency and duration of said sequential interruption intervals.

* * * * *